United States Patent [19]

Löffler

[11] Patent Number: 5,721,789
[45] Date of Patent: Feb. 24, 1998

[54] METHOD FOR TESTING ELASTIC PROPERTIES OF A DRESSING ON A PRINTING CYLINDER

[75] Inventor: Gerhard Löffler, Walldorf, Germany

[73] Assignee: Heidelberger Druckmaschinen AG, Heidelberg, Germany

[21] Appl. No.: 421,189

[22] Filed: Apr. 13, 1995

[30] Foreign Application Priority Data

Apr. 13, 1994 [DE] Germany ............... 44 12 602.6

[51] Int. Cl.$^6$ ........................ G06K 9/00
[52] U.S. Cl. ........................ 382/112; 364/552
[58] Field of Search ........................ 382/112, 270, 382/266; 250/559.01, 208.1, 237.2, 227.28; 364/552, 526

[56] References Cited

U.S. PATENT DOCUMENTS 5,144,566  9/1992  Anderson ........................ 382/112
5,625,703  4/1997  Okuda ........................ 382/112

FOREIGN PATENT DOCUMENTS 36 39 636  5/1988  Germany.
38 05 248 C2  8/1989  Germany.
41 09 938  10/1991  Germany.
42 28 904  3/1994  Germany.

OTHER PUBLICATIONS

Treffpunkt Druckindustrie Publ. Nov. 1994, p. 52, "Automatic Error Detection System".

Primary Examiner—Dwayne Bost
Assistant Examiner—Brian L. Johnson
Attorney, Agent, or Firm—Herbert L. Lerner; Laurence A. Greenberg

[57] ABSTRACT

The object of the invention is attained in a manner where is at least one image pickup device is provided for picking up image signals obtained from at least one surface of a printed image, and a steering and control device connected to the pickup device in which the image sequences are stored. Furthermore, the image signals are examined for presence of jumps or transitions in tone values, and the position coordinates of the transitions in tone value jumps are stored. In a further step the frequency of those tone value jumps, in direction of the coordinates, which exceeds a given threshold value, are recorded, and applied to develop a signal for indicating need to replace the dressing.

3 Claims, 3 Drawing Sheets

METHOD FOR TESTING ELASTIC PROPERTIES OF A DRESSING ON A PRINTING CYLINDER

BACKGROUND OF THE INVENTION

Field of the Invention

The invention relates to a method for testing the elastic properties of a dressing on a transfer cylinder of an offset printing machine in particular for testing the suitability of a rubber printing blanket as a printing transfer element.

In offset printing machines dressings or rubber blankets placed on the transfer cylinders are, during printing, subject to a permanent change in shape, i.e. settling, due to pressure in the printing nip. Rubber blankets become thinner in the regions wherein most frequently sheets or webs of the same format, i.e. of equal width in the printing direction, are printed. The required pressure between the cylinders and the printing material can be readjusted by means of cylinder pressure control devices. Due to the location-limited settling of the rubber blanket, which is especially pronounced with newly installed rubber blankets, and with printing of large numbers of prints, greater pressures become present outside the settling range of the rubber blanket, compared with the pressure in the settling range, by printing of greater web or sheet widths. This leads to different tone value increases and thereby to different contrast outside and inside the aforesaid settling ranges. By means of visual evaluation of the printed image, especially by evaluation of homogeneous halftime values, it can be determined to which degree settling limits are visible from the smaller printing material format. Within the settling range the print shows to be more light than outside the range. When the transition between the lighter printed ranges and the darker printed ranges, i.e. between the more or less saturated ranges in the printed image, exceeds a given threshold, as determined by sensitivity of the evaluating person, the rubber blanket is replaced.

This method has the drawback that the determination of the usefulness of a rubber blanket depends on the sensitivity and experience of the person doing the evaluation with the result that the wear of a rubber blanket may not be determined early enough, or is determined too late, resulting in a great many prints of inadequate quality being printed.

Summary of the Invention

It is accordingly an object of the invention to provide a testing process for continuously monitoring the elastic properties of a dressing on a transfer roller, and which generates a distinct signal indicating the need for replacing the dressing when it has become worn beyond the allowable limit.

The object of the invention is attained in a manner where is at least one image pickup device is provided for picking up image signals obtained from at least one surface of a printed image, and a steering and control device connected to the pickup device in which the image sequences are stored. Furthermore, the image signals are examined for presence of jumps or transitions in tone values, and the position coordinates of the transitions in tone value jumps are stored. In a further step the frequency of those tone value jumps, in direction of the coordinates, which exceeds a given threshold value, are recorded, and applied to develop a signal for indicating need to replace the dressing.

In a variation of the invention the coordinate directions, in which the tone value jumps are exceeding the given tolerances and the given frequency of the jumps exceeding the tolerances are correlated with the also stored print format, i.e. the printing width data, so that, when the distance between the tone value jumps in the coordinate direction are in correlation with the paper format, i.e. the print width data, the signal for replacing the dressing is generated.

The image signals obtained with the image pickup device can be used for continuously detecting a so-called ghost format, by means of which a high degree of confidence and objectivity may be attained in controlling the suitability of the dressing.

In accordance with the inventive concept, there is provided a method for testing the elastic properties of a dressing on a transfer cylinder of an offset printing machine having at least one printed image pickup device for picking up image signals from at least one surface of a printing material in the printing machine, and a steering and control device connected with the image pickup device, the method which includes the steps of storing the image signals in the steering and control device, scanning the image signals stored in the control device for presence of jumps in tone values of the image, storing in the steering and control device position coordinates of the jumps in the tone values, determining with the steering and control device the frequency (H) in the jumps in tone values in regions of the coordinates (X, Y) of the image, determining with the steering and control device of the frequency of the jumps in tone value in the region of one coordinate direction (X, Y) that exceeds a given threshold value ($H_1$), and generating, if (H) exceeds the given threshold value (H1), a signal for replacing the dressing.

According to another feature, there is provided a method which further includes the steps of correlating the coordinate directions (X, Y) in which the tone value jump frequency (H) exceed the given limit value ($H_1$) with the image format; and if the distances ($X_2$–$X_1$) between the tone value jumps correlates with the coordinate directions of the printing material, generating the signal for replacing the dressing.

According to still another feature one of the coordinate directions (X, Y) includes the width of the printing material.

Other features which are considered as characteristic for the invention are set forth in the appended claims.

Although the invention is illustrated and described herein as embodied in method for testing elastic properties of a sheet on a printing cylinder, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
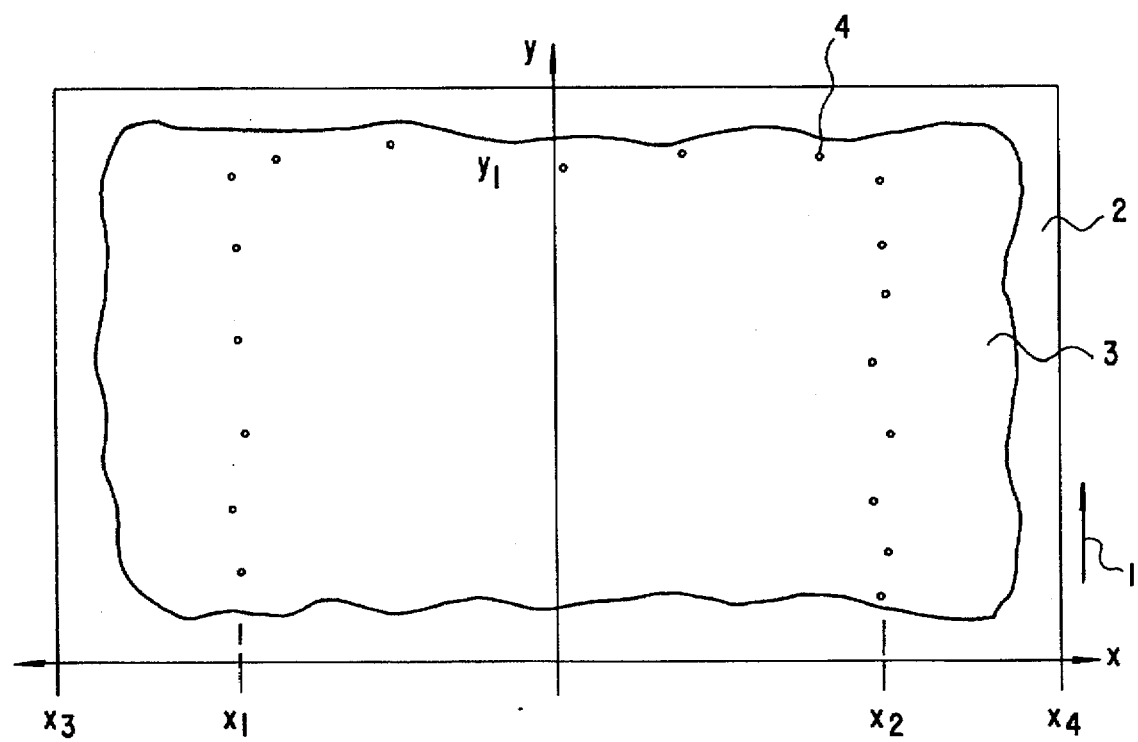
FIG. 1 is a diagrammatic plan view of an unfolded dressing with points of jumps in tone values.

In FIG. 1, as described above, the printing material 2 is moving in direction indicated by arrow 1 in Y-direction of the printing material 2. The printed image has tone value jumps 4 seen along the Y-axis at distances X1 and X2 from the Y-axis. The jumps 4 appear in their respective rows at a certain frequency H measured, e.g. in jumps/meter. When, at a certain maximum allowable frequency H1 of jumps 4, seen in FIG. 2, has been reached, a signal to indicate maximum jump frequency is to be issued.

Figure 2:
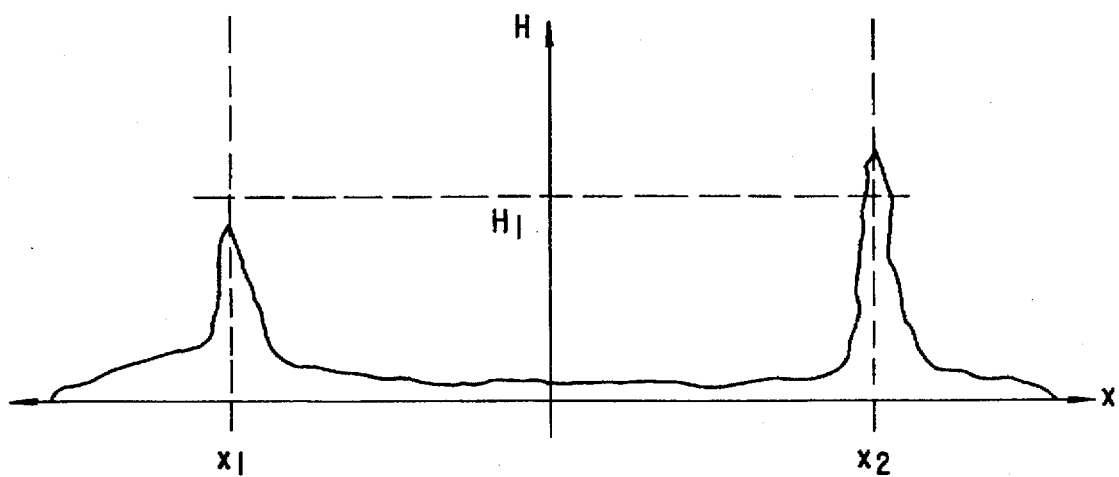
FIG. 2 is a curve of the frequency tone value jumps taken along e.g. the Y-axis at distances $X_1$ and $X_2$ from the Y-axis of the printed image.

As shown in FIG. 2, the frequency of the tone value jumps 4 show a maximum value of jump frequency along the coordinate directions $X_1$ and $X_2$, which are located on the rubber blanket, on which a smaller preferred image format $(X_2-X_1)$ has earlier been frequently printed. The jump frequency along coordinates $X_2$ that exceeds a threshold $H_1$, causes the steering and control device 21 to generate an optical or acoustic signal indicating to the machine operator that replacement of the rubber blanket is to be performed.

Figure 3:
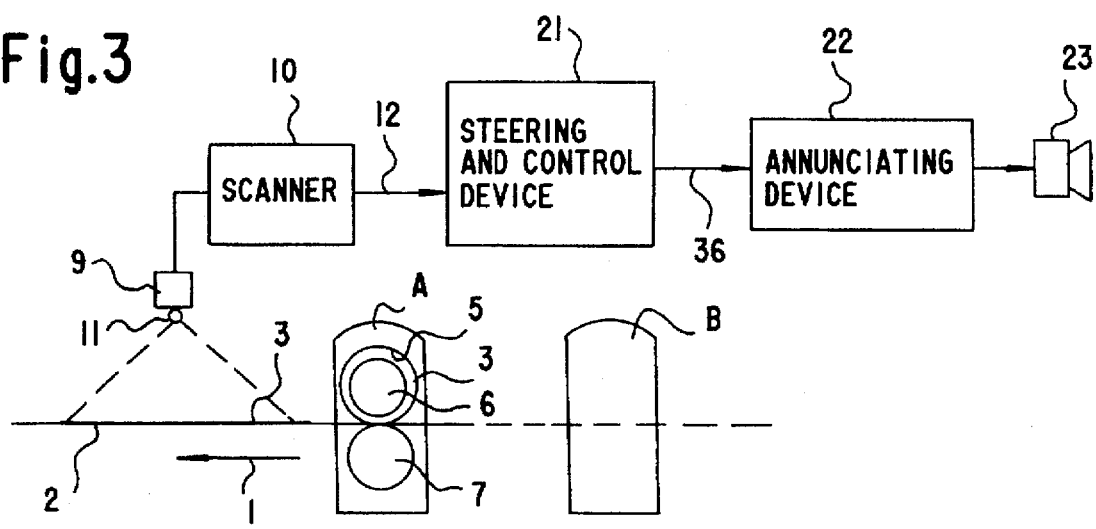
FIG. 3 is a block diagram of parts of an offset printing machine and the major elements of the apparatus for performing the method of the invention.
Figure 4:
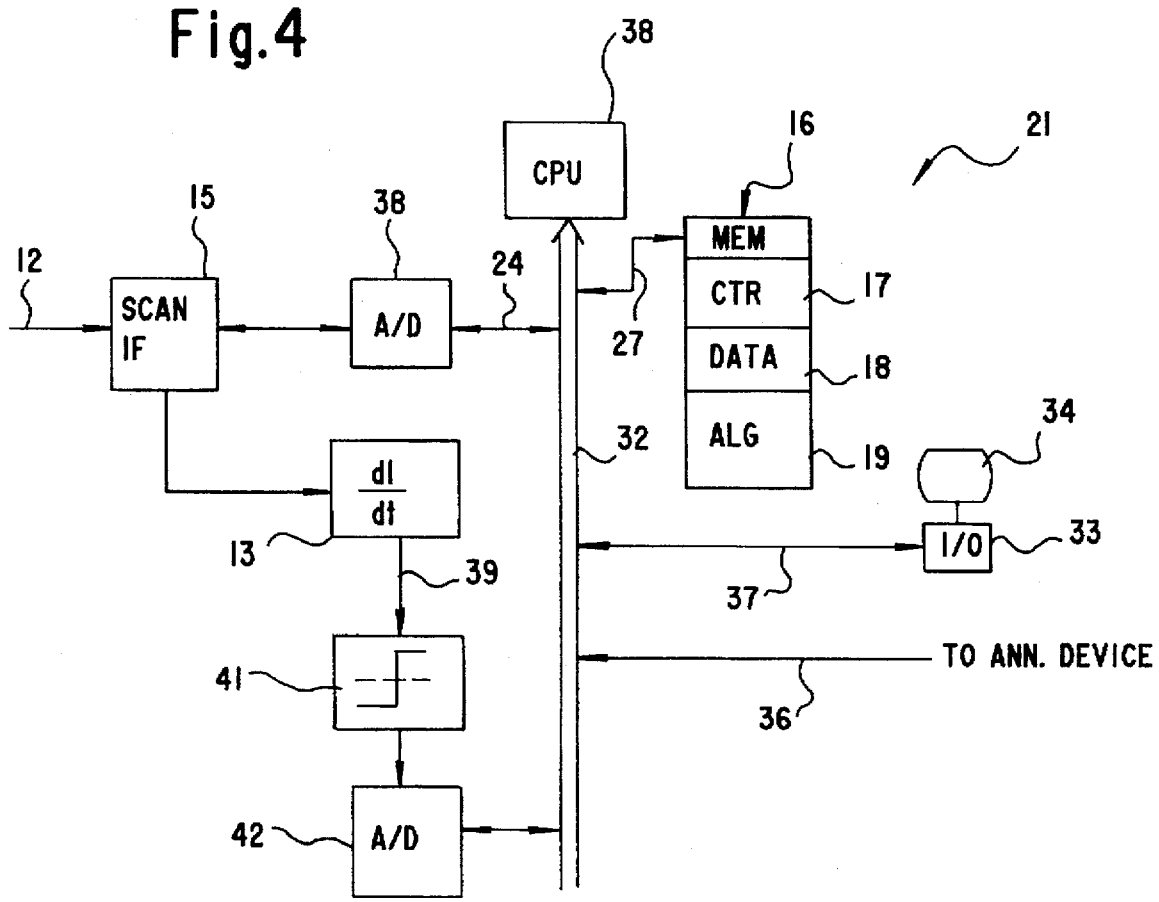
FIG. 4 is a block diagram of the major elements of the steering and control device.

FIG. 3 is a block diagram of a part of a printing machine showing two printing units A and B, and printing material 2 moving from right to left through printing units 3 and A, from which the image 3 is further processed as follows.

As seen in FIG. 3 the multi-color offset printing machine has an image pickup device 9 positioned after the last printing unit A. The image pickup device 9 is directed at the image 3 printed on printing material 2, which passes in direction indicated by arrow 1 under the pickup device 9. The image pickup device 9 is capable of scanning images of all applicable image formats including their border regions. The image pickup device 9 scans the surface of the printing material and generates a string of image signals on lead 12 which are transmitted to a steering and control device 21 (FIG. 3), which further processes the image signals to detect the aforesaid ghost image. To that end tone value jumps and their frequency in the coordinate directions is detected. In FIG. 1 the coordinate direction Y is oriented in the moving direction 1 of the sheet or printing material 2 and coordinate direction X is perpendicular thereto. The width $(X_4-X_3)$ of the printing material 2 is greater than the earlier printed sheets $(X_2-X_1)$. The printed image 3 shows the contrasting tone value jumps 4, the coordinates of which are obtained by means of the steering and control device 21. At the same time the frequency of tone value jumps, measured e.g. in jumps per meter is computed in the coordinate directions X, Y in the steering and control device 21.

FIG. 3 shows in printing unit A a transfer roller 6 having a rubber blanket 3 wrapped around its circumference 5. Other rollers, not shown for the sake of clarity, transfer an image to be printed to the surface of the rubber blanket 3, which in turn transfers the inked image to the printing material 2.

The image pickup device 9 scans the image 3 under control of a scanner 10, which directs a scanning beam in the image pickup device 9, to scan all prints of the image 3 in conventional image scanning manner. The image signals include position information and tone values as sensed by the scanning beam, and are transmitted via connection 12 to the steering and control device 21, wherein the signals are stored.

The steering and control device 21 is shown in more detail in FIG. 3, wherein a scanning interface 15 receives the image signals and position information. The image signals are converted to digital format in a first A/D converter 38. The digital position information is transmitted via a data connection and a data bus 32, under control of a central processing unit (CPU) 38 to a memory 16, wherein it is stored in a data memory section 18.

The analog image signals from the image pickup device 9 are branched off from the scanner interface 15 to a differentiating filter dI/dt circuit 13, which in conventional manner differentiates the image signals. The differentiation filter circuit 13 generates an output signal 39 whenever a concentration in tonal value of the image, i.e. a tonal value jump is encountered by the scanning beam. The differentiated image signal is processed in a threshold device, e.g. a Schmitt trigger 41, which is in turn connected to a second A/D converter 42, from where the jump parameters are transmitted in digital form via the data bus, under control of the CPU 38 to the data memory section 18, in which a jump map is created of all the tone value jumps 4, corresponding to the image shown in FIG. 1.

A control program, stored in control memory section (CTR) 17 performs on the basis of the map stored in data memory section 18, a computation of the frequency H of tone value jumps along the coordinates X and Y, and compares the frequency H with the maximum allowable frequency value H1. In case the frequency value exceeds value H1, a signal indicating replacement of the rubber blanket is transmitted via connection 36 to an annunciating device 22 (FIG. 3), which in turn activates e.g., an acoustic device 23, or an optical display, e.g. in the form of a computer screen 36, connected with a manual input/out device (I/O) 33.

A memory algorithm, section 19, serves to store computational algorithms as required by the CPU 38 to perform calculations such as the frequency of the tone value jumps 4, and the like.

Figure 5:
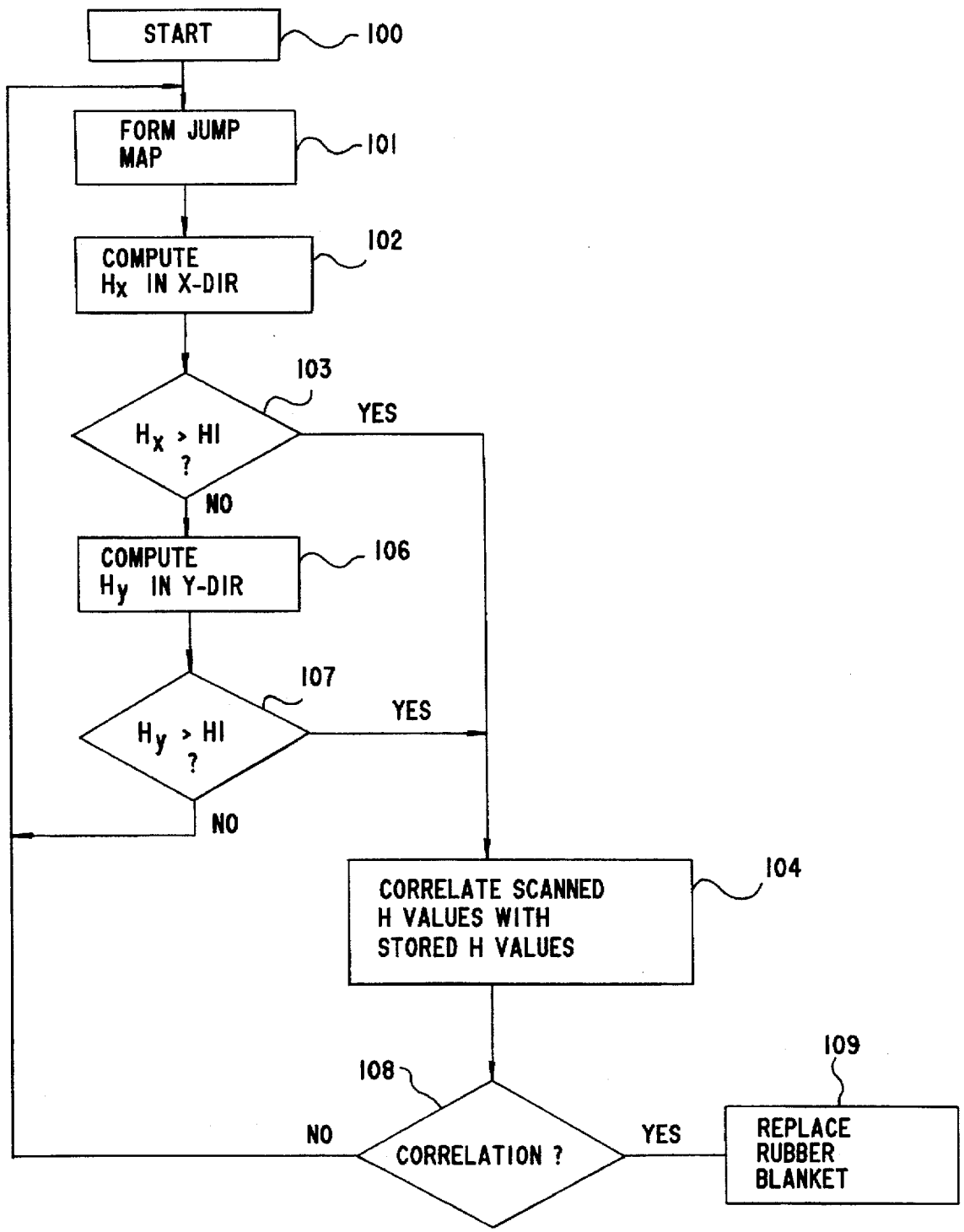
FIG. 5 is a flowchart showing the major steps of the method according to the invention.

In FIG. 5 the steps of determining whether to replace the rubber blanket is shown. After start 100, a map of all jumps in tonal value is formed in memory in step 101. In step 102 the frequency $H_x$ of jumps in direction of the X coordinates is computed. In decision step 103, the $H_x$ values are compared with the maximum frequency limit $H_1$. If affirmative, correlation with earlier computed values is performed in step 104. If correlation is affirmed in step 108, a signal to replace the rubber blanket is issued in step 109.

In case the decision in step 103 is negative, the frequency $H_y$ is computed in Y coordinate direction in step 106, and compared with $H_1$, in decision step 107. If affirmative in step 107, correlation with stored H values is again made in step 104, and if affirmative in decision step 108, a rubber blanket replacement signal is generated in step 109.

If the decisions are negative in decision steps 107 and 108, the process returns to step 101, wherein a new map is formed, and the process is repeated.

I claim:

1. A method for testing elastic properties of a dressing on a transfer cylinder of an offset printing machine having at least one printed image (3) pickup device (9) for picking up image signals from at least one surface of a printing material (2) in the printing machine, and a steering and control device (21) connected with the image pickup (9) device, the method comprising:

storing the image signals in the steering and control device (21);

scanning the image signals for presence of jumps (4) in tone values of the image;

storing in the steering and control device (21) position coordinates of the jumps (4) in the tone values;

determining with the steering and control device (21) a frequency (H) in the jumps in tone values in regions of coordinates (X,Y) of the image;

determining with the steering and control device (21) if the frequency (H) of the jumps in tone value in a region of one coordinate direction (X,Y) exceeds a given value ($H_1$); and generating, if affirmative, a signal for replacing the dressing.

2. A method according to claim 1, further comprising:

correlating the coordinate directions (X, Y) in which the tone value jump frequency (H) exceed the given limit value ($H_1$) with the image format; and if distances ($X_2-X_1$) between the tone value jumps (H) correlates with the coordinate directions of the printing material, generating the signal for replacing the dressing.

3. A method according to claim 1, wherein one of the coordinate directions (X, Y) includes a width of the printing material.

* * * * *